(12) United States Patent
Hiraoka et al.

(10) Patent No.: US 8,871,245 B2
(45) Date of Patent: Oct. 28, 2014

(54) TRANSDERMAL PATCH

(75) Inventors: Takao Hiraoka, Bunkyo-ku (JP); Shuta Nakanami, Bunkyo-ku (JP); Toru Koga, Bunkyo-ku (JP)

(73) Assignee: Nichiban Co., Ltd., Tokyo (JP)

( * ) Notice: Subject to any disclaimer, the term of this patent is extended or adjusted under 35 U.S.C. 154(b) by 0 days.

(21) Appl. No.: 13/581,673

(22) PCT Filed: Feb. 28, 2012

(86) PCT No.: PCT/JP2012/054907
§ 371 (c)(1),
(2), (4) Date: Oct. 1, 2012

(87) PCT Pub. No.: WO2013/128562
PCT Pub. Date: Sep. 6, 2013

(65) Prior Publication Data
US 2013/0220846 A1    Aug. 29, 2013

(51) Int. Cl.
*A61F 13/00* (2006.01)
*A61K 9/14* (2006.01)
*A61K 31/27* (2006.01)

(52) U.S. Cl.
USPC ............................ 424/443; 424/487; 514/490

(58) Field of Classification Search
None
See application file for complete search history.

(56) References Cited

U.S. PATENT DOCUMENTS

| | | | |
|---|---|---|---|
| 4,077,926 A * | 3/1978 | Sanderson et al. | 524/558 |
| 6,143,319 A * | 11/2000 | Meconi et al. | 424/448 |
| 2007/0128263 A1 | 6/2007 | Gargiulo et al. | |
| 2008/0138388 A1 | 6/2008 | Aida et al. | |
| 2010/0087768 A1* | 4/2010 | Forlano et al. | 602/48 |
| 2011/0066120 A1 | 3/2011 | Lee | |

FOREIGN PATENT DOCUMENTS

| | | |
|---|---|---|
| CN | 101312717 A | 11/2008 |
| EP | 2 298 277 A1 | 3/2007 |
| EP | 1 959 937 | 8/2008 |
| EP | 2 172 194 A1 | 4/2010 |
| EP | 2 286 802 A1 | 2/2011 |
| EP | 2 292 219 A1 | 3/2011 |
| JP | A-9-503756 | 4/1997 |
| JP | A-2002-500178 | 1/2002 |
| JP | A-2009-517468 | 4/2009 |
| KR | 10-2008-0071581 A | 8/2008 |
| WO | WO 2006/082728 A1 | 8/2006 |
| WO | WO 2007/064407 A1 | 6/2007 |
| WO | WO 2011/029598 A1 | 3/2011 |
| WO | WO 2011/076621 A2 | 6/2011 |

OTHER PUBLICATIONS

Scientific Discussion, Exelon (Sep. 17, 2007), pp. 1-19.*
Written Opinion of the International Searching Authority dated Apr. 3, 2012 from International Application No. PCT/JP2012/054907.
Oertel et al; "Rationale for transdermal drug administration in Alzheimer disease;" Neurology; 2007; vol. 69, No. Suppl 1; pp. S4-S9.
Roed-Petersen et al; "Contact dermatitis from antioxidants;" British Journal of Dermatology; 1976; vol. 94; p. 233-241.
Apr. 3, 2012 International Search Report issued in International Application No. PCT/JP2012/054907 (with translation).

\* cited by examiner

*Primary Examiner* — Scott Long
*Assistant Examiner* — Lyndsey Beckhardt
(74) *Attorney, Agent, or Firm* — Oliff PLC

(57) ABSTRACT

A transdermal patch for the treatment of Alzheimer's disease includes: a backing, a rivastigmine-containing layer, a pressure-sensitive adhesive layer, and a release liner. In the transdermal patch, the rivastigmine-containing layer contains rivastigmine and an alkyl (meth)acrylate resin, the pressure-sensitive adhesive layer is composed of an acrylic pressure-sensitive adhesive containing a (meth)acrylic acid ester having a hydroxy group, and neither the rivastigmine-containing layer nor the pressure-sensitive adhesive layer contains an anti-oxidizing agent.

14 Claims, No Drawings

TRANSDERMAL PATCH

TECHNICAL FIELD

The present invention relates to a transdermal patch containing rivastigmine, and specifically relates to a transdermal patch for the treatment of Alzheimer's disease including two layers composed of a rivastigmine-containing layer and an acrylic pressure-sensitive adhesive layer.

BACKGROUND ART

Rivastigmine is one of the acetylcholine esterase inhibitors and is used as a therapeutic agent for Alzheimer's dementia (anti-dementia drug).

For such an anti-dementia drug, oral administration such as a tablet, a capsule, syrup, and granules, and administration by injection or through the rectum have been studied depending on a medicinal agent or a disease condition. In recent years, transdermal administration, that is, administration using a transdermal patch has also been developed for such an anti-dementia drug.

It is considered that the rivastigmine is relatively easily oxidized, and it is indicated that decomposition products of the rivastigmine may increase with time. To address this, a technique of adding an anti-oxidizing agent into a transdermal patch containing the rivastigmine has been developed (for example, Patent Document 1 and Patent Document 2). Patent Document 2 discloses a preparation in which a storage layer containing the rivastigmine is laminated to a silicone pressure-sensitive adhesive. However, the silicone pressure-sensitive adhesive itself is expensive and a release liner for such a silicone pressure-sensitive adhesive needs special treatment. Hence, the preparation has a problem of high cost.

Each transdermal patch disclosed in Patent Document 1 and Patent Document 2 uses an acrylic pressure-sensitive adhesive containing a carboxy group. However, the use of such an acrylic pressure-sensitive adhesive is considered to affect the oxidation of the rivastigmine to not a little extent. To address this, there is a report that the use of a pressure-sensitive adhesive having no carboxy group and no hydroxy group as the acrylic pressure-sensitive adhesive enables the formation of a transdermal patch excellent in temporal stability of the rivastigmine (Patent Document 3).

In order to improve skin permeability of the rivastigmine or to reduce skin irritation caused by a pressure-sensitive adhesive layer, a transdermal patch using a hydroxy group-containing acrylate-rubber hybrid pressure-sensitive adhesive (Patent Document 4) and a transdermal patch including an acrylic pressure-sensitive adhesive layer that has a hydroxy group, etc. and that contains a nonvolatile substance such as citric acid in order to reduce the loss of an active substance (medicinal agent) due to vaporization in the production process (Patent Document 5) have been developed. However, there is no discussion on the stability of the rivastigmine in these documents.

RELATED ART DOCUMENTS

Patent Documents

Patent Document 1: Japanese Translation of PCT International Application Publication No. JP-T-2002-500178
Patent Document 2: Japanese Translation of PCT International Application Publication No. JP-T-2009-517468
Patent Document 3: International Publication WO 2011/076621 pamphlet
Patent Document 4: U.S. Patent Application Publication No. 2011/0066120 specification
Patent Document 5: European Patent No. 2172194 specification
Patent Document 6: Japanese Translation of PCT International Application Publication No. JP-T-9-503756

Non-Patent Document

Non-Patent Document 1: JYTTE ROED-PERERSEN et al.: Contact dermatitis from antioxidants HIDDEN SENSITIZERS IN TOPICAL MEDICATIONS AND FOODS, British Journal of Dermatology (1976) 94, 233.

SUMMARY OF THE INVENTION

Problem to be Solved by the Invention

As described above, in order to solve the temporal instability of the rivastigmine due to oxidation, the addition of an anti-oxidizing agent and the use of a pressure-sensitive adhesive having no carboxy group and no hydroxy group have been developed. Thus, in a transdermal patch using an acrylic pressure-sensitive adhesive containing a hydroxy group, the skin permeability of the rivastigmine must be improved. Also, the stability of the rivastigmine must be improved in another manner because the pressure-sensitive adhesive layer used is considered to be unfavorable from the viewpoint of oxidation stability. There is another demand for a transdermal patch containing no anti-oxidizing agent, because adding an anti-oxidizing agent may cause skin irritation (Non-Patent Document 1).

In the production of a conventional transdermal patch containing the rivastigmine, a layer containing the medicinal agent and a pressure-sensitive adhesive is typically formed by a spread coating method (a production method including forming a layer containing a medicinal agent and a pressure-sensitive adhesive by coating followed by a heating and drying process). However, in the spread coating method, an additive for inhibiting the vaporization of a medicinal agent is added as described in Patent Document 5, a coating is dried at a drying temperature of 60° C. or higher (for example, Patent Document 4 and Patent Document 5), or a medicinal agent is added to a pressure-sensitive adhesive layer in an amount that is a certain amount more than necessary in advance, that is, "excess addition" is performed, on the assumption that the medicinal agent is volatilized during production. Such a method doest not consider the effect of the "heating" (oxidation, etc.) during the production process of a transdermal patch. Therefore, there is a room for improvement in the production method of the transdermal patch for improving the temporal stability of the rivastigmine.

The present inventors provide a transdermal patch containing the rivastigmine, which allows desired adhesive properties to be thoroughly obtained as well as has good temporal stability of the rivastigmine without using an anti-oxidizing agent. In addition, the transdermal patch can be produced easily and with reduced cost.

Means for Solving the Problem

The present inventors have carried out intensive studies in order to solve the problems described above and have studied the structure of a transdermal patch having excellent temporal stability of the rivastigmine without using an anti-oxidizing agent. The present inventors have searched the structure of a transdermal patch that can be produced by a so-called "ointment coating method" while avoiding a heating process that may impair the stability of the rivastigmine, as much as possible. As a result, the present inventors have developed a structure in which a medicinal agent-containing layer and a pressure-sensitive adhesive-containing layer are separated, that is, a two-layer structure composed of a rivastigmine-containing layer and a pressure-sensitive adhesive layer including a particular acrylic pressure-sensitive adhesive on a backing, and have found that the structure can solve the problems, and the present invention has been accomplished.

That is, the present invention relates to a transdermal patch for the treatment of Alzheimer's disease. The transdermal patch includes a backing, a rivastigmine-containing layer provided on the backing, a pressure-sensitive adhesive layer provided on the rivastigmine-containing layer, and a release liner; or includes a backing, a pressure-sensitive adhesive layer provided on the backing, a rivastigmine-containing layer provided on the pressure-sensitive adhesive layer, and a release liner. In the transdermal patch, the rivastigmine-containing layer contains rivastigmine and an alkyl (meth)acrylate resin, the pressure-sensitive adhesive layer is composed of an acrylic pressure-sensitive adhesive containing a (meth) acrylic acid ester having a hydroxy group, and neither the rivastigmine-containing layer nor the pressure-sensitive adhesive layer contains an anti-oxidizing agent.

The present invention further provides embodiments below.
1. In the transdermal patch for the treatment of Alzheimer's disease, the rivastigmine-containing layer is a layer formed by using a solution containing the rivastigmine under a condition at 1° C. or higher and lower than 60° C.
2. In the transdermal patch for the treatment of Alzheimer's disease, the rivastigmine-containing layer contains the rivastigmine in an amount of 20% to 95% by mass based on a total mass of the layer.
3. In the transdermal patch for the treatment of Alzheimer's disease, the rivastigmine-containing layer is a layer having a thickness of 10 μm to 80 μm and the pressure-sensitive adhesive layer is a layer having a thickness of 10 μm to 100 μm.

The present invention also relates to a method for producing a transdermal patch for the treatment of Alzheimer's disease. The method includes 1) a rivastigmine layer formation step of applying a solution containing rivastigmine onto a backing to form a rivastigmine-containing layer, a pressure-sensitive adhesive layer formation step of applying a solution containing an acrylic pressure-sensitive adhesive onto a release liner to form a pressure-sensitive adhesive layer, and a transdermal patch formation step of bonding the rivastigmine-containing layer formed on the backing to the pressure-sensitive adhesive layer formed on the release liner, includes ii) a pressure-sensitive adhesive layer formation step of applying a solution containing an acrylic pressure-sensitive adhesive onto a backing to form a pressure-sensitive adhesive layer, a rivastigmine layer formation step of applying a solution containing rivastigmine onto a release liner to form a rivastigmine-containing layer, and a transdermal patch formation step of laminating the pressure-sensitive adhesive layer formed on the backing to the rivastigmine-containing layer formed on the release liner, or includes iii) a pressure-sensitive adhesive layer formation step of applying a solution containing an acrylic pressure-sensitive adhesive onto a backing to form a pressure-sensitive adhesive layer, a rivastigmine layer formation step of applying a solution containing rivastigmine onto the pressure-sensitive adhesive layer to form a rivastigmine-containing layer, and a transdermal patch formation step of laminating the rivastigmine-containing layer formed on the pressure-sensitive adhesive layer on the backing to a release liner. In the method, the solution containing rivastigmine contains the rivastigmine and an alkyl (meth) acrylate resin, the solution containing an acrylic pressure-sensitive adhesive contains an acrylic pressure-sensitive adhesive containing a (meth)acrylic acid ester having a hydroxy group, and neither the solution containing rivastigmine nor the solution containing an acrylic pressure-sensitive adhesive contains an anti-oxidizing agent.

The present invention further provides embodiments below.
4. In the method, the rivastigmine-containing layer formation step includes applying the solution containing rivastigmine onto the backing under a temperature condition of 1° C. or higher and lower than 60° C.
5. The method further includes a cooling step of allowing the pressure-sensitive adhesive layer to cool or forced-cooling the pressure-sensitive adhesive layer, after the pressure-sensitive adhesive layer formation step and before the transdermal patch formation step.
6. The method further includes an aging step before and after the cooling step.

The present invention further relates to a product of a transdermal patch for the treatment of Alzheimer's disease produced by sealing the transdermal patch for the treatment of Alzheimer's disease or a transdermal patch for the treatment of Alzheimer's disease produced by the method in a package composed of a laminate of multi-layered films or multi-layered sheets. The transdermal patch product has aspects below.
6. In the transdermal patch product, an innermost layer of the package is a layer containing polyacrylonitrile as a main component.
7. In the transdermal patch product, the package includes a film or a sheet having a layer containing an oxygen absorber or an oxygen absorber is separately enclosed in the package.
8. In the transdermal patch product, an atmosphere in the package is substituted and filled with nitrogen.

The present invention also relates to a transdermal patch for the treatment of Alzheimer's disease that includes a polyester film backing, a rivastigmine-containing layer provided on the backing, a pressure-sensitive adhesive layer provided on the rivastigmine-containing layer, and a release liner. In the transdermal patch, the rivastigmine-containing layer contains rivastigmine and an alkyl (meth)acrylate resin, the pressure-sensitive adhesive layer includes an acrylic pressure-sensitive adhesive containing a (meth)acrylic acid ester having a hydroxy group, neither the rivastigmine-containing layer nor the pressure-sensitive adhesive layer contains an anti-oxidizing agent or an acrylic pressure-sensitive adhesive containing a (meth)acrylic acid ester having a carboxy group, and the transdermal patch includes a degradation product of the rivastigmine in a total amount of less than 0.50% by mass based on an amount of the rivastigmine after storage under a severe condition (60° C.) for two weeks from a production date of the transdermal patch.

Effect of the Invention

The present invention can provide a transdermal patch that has excellent practical performance. The transdermal patch is configured by providing two layers, i.e., a rivastigmine-containing layer and a pressure-sensitive adhesive layer having an acrylic pressure-sensitive adhesive, on a backing. Thus, even without using an anti-oxidizing agent and even when an acrylic pressure-sensitive adhesive containing a hydroxy group that may affect the oxidation of the rivastigmine is used as the pressure-sensitive adhesive, the transdermal patch can suppress the formation of degradation products of the rivastigmine after the production of the transdermal patch, has excellent temporal stability of the rivastigmine, and has adhesive properties required for a transdermal patch.

The addition of the alkyl (meth)acrylate resin into the rivastigmine-containing layer enables the formation of a rivastigmine-containing layer having excellent adhesive properties to the backing and excellent attaching properties to a skin. The use of the acrylic pressure-sensitive adhesive containing a (meth)acrylic acid ester having a hydroxy group as the pressure-sensitive adhesive enables the formation of a pressure-sensitive adhesive layer having excellent attaching properties to a skin and excellent adhesive properties to the backing.

The use of the rivastigmine-containing layer formed at a certain temperature or lower can provide a transdermal patch eliminating the oxidation effect on the rivastigmine due to temperature.

The production method of the present invention does not require a heating and stirring process or a heating and drying process, or the like for the formation of the rivastigmine-containing layer. With this method, it is possible to produce a transdermal patch while eliminating high temperature heating processes that can affect the oxidation of the rivastigmine as many as possible during the production of the transdermal patch.

Therefore, in the obtained transdermal patch, the formation of rivastigmine degradation products due to heat is suppressed during the production of the transdermal patch, and the method enables the formation of a transdermal patch having excellent stability of the rivastigmine.

In addition, the transdermal patch of the present invention does not need "excess addition", that is, adding a medicinal agent in an amount that is a certain amount more than necessary in advance, and does not include an anti-oxidizing agent, which enables cost reduction.

MODES FOR CARRYING OUT THE INVENTION

The transdermal patch for the treatment of Alzheimer's disease of the present invention is composed of a backing, a rivastigmine-containing layer, a pressure-sensitive adhesive layer, and a release liner, and is characterized in that neither the rivastigmine-containing layer nor the pressure-sensitive adhesive layer contains any anti-oxidizing agent.

The transdermal patch of the present invention has a specific structure composed of the rivastigmine-containing layer provided on the backing, the pressure-sensitive adhesive layer provided on the rivastigmine-containing layer, and the release liner or a specific structure composed of the backing, the pressure-sensitive adhesive layer provided on the backing, the rivastigmine-containing layer provided on the pressure-sensitive adhesive layer, and the release liner.

[Rivastigmine-Containing Layer]

In the transdermal patch of the present invention, the rivastigmine-containing layer contains rivastigmine and an alkyl (meth)acrylate resin.

The rivastigmine ((S)—N-ethyl-3-[1-(dimethylamino)ethyl]-N-methyl-phenyl-carbamate) used in the present invention may be either in a free base form or in an acid addition salt form.

The amount of the rivastigmine contained is not particularly limited, but is, for example, 20% to 95% by mass, preferably 30% to 90% by mass, and more preferably 35% to 90% by mass, based on the total mass of the rivastigmine-containing layer.

The amount of the rivastigmine contained is, for example, 10% to 40% by mass, preferably 10% to 35% by mass, and more preferably 10% to 25% by mass, based on the total mass of the rivastigmine-containing layer and the pressure-sensitive adhesive layer described later.

The alkyl (meth)acrylate resin contained in the rivastigmine-containing layer works as a thickener and includes alkyl (meth)acrylate copolymers and acrylic pressure-sensitive adhesives containing a (meth)acrylic acid ester.

Specific examples of the alkyl (meth)acrylate copolymer include a methyl methacrylate-butyl methacrylate-dimethylaminoethyl methacrylate copolymer, a methacrylic acid-methyl methacrylate copolymer, a methacrylic acid-ethyl acrylate copolymer, an ethyl acrylate-methyl methacrylate copolymer, and a butyl methacrylate-methyl methacrylate copolymer. The weight average molecular weight of the alkyl (meth)acrylate copolymer is not particularly limited, but is 10,000 to 300,000 and preferably 100,000 to 200,000.

For such a copolymer, a commercial product may be appropriately used, and for example, Eudragit (registered trademark, manufactured by Evonik Rohm GmbH) products can be suitably used. Specific examples of the commercial product include Eudragit E100, Eudragit EPO, Eudragit L100, Eudragit L100-55, Eudragit S100, Eudragit RL100, Eudragit RLPO, Eudragit RS100, Eudragit RSPO, and Plastoid B.

Among these Eudragit products, Eudragit EPO is especially preferred from the viewpoints of miscibility with the rivastigmine and adhesive properties to a backing.

Specifically, the acrylic pressure-sensitive adhesive containing a (meth)acrylic acid ester is preferably a polymer obtained by copolymerization of one or more alkyl esters of (meth)acrylic acid as main monomer components with one or more optional copolymerizable monomers (for example, 2-ethylhexyl acrylate, vinylpyrrolidone, vinyl acetate, methoxyethyl acrylate, hydroxyethyl acrylate, and acrylic acid). Here, examples of the alkyl (meth)acrylate include alkyl acrylates such as methyl acrylate, ethyl acrylate, isopropyl acrylate, n-butyl acrylate, t-butyl acrylate, isoamyl acrylate, 2-ethylhexyl acrylate, n-octyl acrylate, isooctyl acrylate, isononyl acrylate, decyl acrylate, and dodecyl acrylate; and alkyl methacrylates such as methyl methacrylate, ethyl methacrylate, n-butyl methacrylate, isobutyl methacrylate, t-butyl methacrylate, isoamyl methacrylate, 2-ethylhexyl methacrylate, n-octyl methacrylate, isooctyl methacrylate, isononyl methacrylate, decyl methacrylate, and dodecyl methacrylate. These alkyl (meth)acrylates may be used singly or in combination of two or more of them. For example, n-butyl acrylate may be used in combination with methyl methacrylate. The weight average molecular weight of the (meth)acrylic acid ester used for the acrylic pressure-sensitive adhesive containing a (meth)acrylic acid ester is not particularly limited, but is 100,000 to 1,000,000.

It is preferable that the acrylic pressure-sensitive adhesive containing a (meth)acrylic acid ester do not substantially include a component containing both a hydroxy group and a carboxy group. Even when the acrylic pressure-sensitive adhesive includes the component containing both a hydroxy group and a carboxy group, the component is preferably included in an amount of 5% by mass or less based on the total mass of the acrylic pressure-sensitive adhesive.

The amount of the alkyl (meth)acrylate resin included is not particularly limited. In the case of the alkyl (meth)acrylate copolymer, the amount is, for example, 5% to 25% by mass, preferably 5% to 20% by mass, and more preferably 5% to 15% by mass, based on the total mass of the rivastigmine-containing layer. In the case of the acrylic pressure-sensitive adhesive containing a (meth)acrylic acid ester, the amount is, for example, 20% to 90% by mass, preferably 30% to 85% by mass, and more preferably 40% to 80% by mass, based on the total mass of the rivastigmine-containing layer.

Based on the total mass of the rivastigmine-containing layer and the pressure-sensitive adhesive layer described later, in the case of the alkyl (meth)acrylate copolymer, the amount of the alkyl (meth)acrylate resin included is, for example, 0.5% to 5.0% by mass, preferably 1.0% to 4.0% by mass, and more preferably 1.0% to 3.0% by mass. In the case of the acrylic pressure-sensitive adhesive containing the (meth)acrylic acid ester, the amount is, for example, 40% to 90% by mass, preferably 50% to 90% by mass, and more preferably 60% to 90% by mass.

In the present invention, the rivastigmine-containing layer may further include an additional additive such as a softener (plasticizer) and an inorganic filler, if desired.

When the additional additive is included, the amount thereof is, for example, 0% to 30% by mass and preferably 0% to 20% by mass based on the total mass of the rivastigmine-containing layer. The amount of the additional additive included is, for example 0% to 20% by mass and preferably 0% to 10% by mass based on the total mass of the rivastigmine-containing layer and the pressure-sensitive adhesive layer described later.

[Pressure-Sensitive Adhesive Layer]

The pressure-sensitive adhesive layer used in the transdermal patch of the present invention is composed of an acrylic pressure-sensitive adhesive containing a (meth)acrylic acid ester having a hydroxy group.

Specifically, the acrylic pressure-sensitive adhesive is preferably a polymer obtained by copolymerization of one or more hydroxyalkyl esters of (meth)acrylic acid with one or more optional copolymerizable monomers (for example, 2-ethylhexyl acrylate, vinylpyrrolidone, vinyl acetate, methoxyethyl acrylate, hydroxyethyl acrylate, and acrylic acid).

Here, examples of the hydroxyalkyl (meth)acrylate include an ester obtained from a hydroxy group-containing primary to tertiary alcohol having a $C_{2-18}$ alkyl group and acrylic acid or methacrylic acid. Specific examples of the hydroxyalkyl (meth)acrylate include 2-hydroxyethyl acrylate, 2-hydroxypropyl acrylate, 3-hydroxypropyl acrylate, 4-hydroxybutyl acrylate, 2-hydroxyethyl methacrylate, 2-hydroxypropyl methacrylate, 3-hydroxypropyl methacrylate, and 4-hydroxybutyl methacrylate.

As the acrylic pressure-sensitive adhesive containing the acrylic acid ester having a hydroxy group, a commercial product such as DURO-TAK (registered trademark) 87-202A, DURO-TAK 87-208A, DURO-TAK 87-2510, DURO-TAK 87-208A, DURO-TAK 87-2287, DURO-TAK 87-4287, DURO-TAK 87-2516, and DURO-TAK 87-2525 (Henkel) may be suitably used.

It is preferable that the pressure-sensitive adhesive layer do not substantially include an acrylic pressure-sensitive adhesive containing a carboxy group as the acrylic pressure-sensitive adhesive. Even when the layer includes the acrylic pressure-sensitive adhesive containing a carboxy group, the acrylic pressure-sensitive adhesive containing a carboxy group is preferably included in an amount of 5% by mass or less based on the total mass of the pressure-sensitive adhesive layer.

In the present invention, the mass ratio of the pressure-sensitive adhesive layer is, for example, 40% to 95% by mass, preferably 50% to 90% by mass, and more preferably 60% to 90% by mass, in the total mass of the rivastigmine-containing layer above and the pressure-sensitive adhesive layer.

In the present invention, the pressure-sensitive adhesive layer may further include an additional additive such as an additional medicinal agent, a tackifier, a cross-linking agent, a softener (plasticizer), an absorption enhancer, polyhydric alcohols, silicone oils, an inorganic filler, and an ultraviolet absorber.

Examples of the tackifier include terpene tackifiers, terpene phenol tackifiers, coumarone indene tackifiers, styrene tackifiers, rosin tackifiers, xylene tackifiers, phenol tackifiers, and petroleum tackifiers.

Various cross-linking agents may be further added into the pressure-sensitive adhesive layer in order to increase a cohesive power of the acrylic pressure-sensitive adhesive. Examples of the cross-linking agent include multifunctional isocyanate compounds, multifunctional epoxy compounds, and polyvalent metal salts. Polyisocyanates [for example, CORONATE (registered trademark) HL (hexamethylene diisocyanate HDI-TMP adduct, manufactured by Nippon Polyurethane Industry Co., Ltd.)] is specifically preferred. Usable examples of the filler include calcium carbonate, magnesium carbonate, silicates, zinc oxide, titanium oxide, magnesium sulfate, and calcium sulfate.

Examples of the absorption enhancer include terpene oils such as d-limonene; fatty acid esters such as glycerin monolaurate, glycerin monooleate, and diethyl sebacate; and fatty acids such as Azone, Pirotiodecane, oleic acid, lauric acid, and myristic acid and derivatives of them.

These additives are optionally added. The amount of the additional additive is, for example 0% to 40% by mass and preferably 0% to 30% mass based on the total mass of the pressure-sensitive adhesive layer and the rivastigmine-containing layer above.

[Backing]

Examples of the backing used in the transdermal patch of the present invention include flexible backings such as films, nonwoven fabrics, Japanese papers, cotton fabrics, knitted fabrics, woven fabrics, and laminated composite bodies of a nonwoven fabric and a film. Such a backing is preferably composed of a soft material that can be in close contact with a skin and can follow skin movement and of a material that can suppress skin rash and other trouble after the transdermal patch is attached for a long time. Examples of the backing material include a material containing, as an essential component, polyethylene, polypropylene, polyethylene terephthalate, polybutylene terephthalate, polyethylene naphthalate, polystyrene, nylon, cotton, acetate rayon, rayon, a rayon/polyethylene terephthalate composite body, polyacrylonitrile, polyvinyl alcohol, acrylic polyurethane, ester polyurethane, ether polyurethane, a styrene-isoprene-styrene copolymer, a styrene-butadiene-styrene copolymer, a styrene-ethylene-propylene-styrene copolymer, styrene-butadiene rubber, an ethylene-vinyl acetate copolymer, or cellophane, for example.

A preferred backing does not adsorb a medicinal agent and does not release a medicinal agent (rivastigmine). In order to suppress the adsorption and release of the medicinal agent, to improve transdermal absorbability of the medicinal agent, and to suppress skin rash and other trouble, the backing preferably includes one or more layers composed of the material above and has a water vapor permeability in a certain range. Specifically, the backing preferably has a water vapor permeability (measured at 40° C. and 90% RH in accordance with JIS Z0208) of 300 g/m²·24 hr or less and particularly 50 g/m²⁰·24 hr or less. The use of a backing having a water vapor permeability within the range can increase skin permeability of the rivastigmine and can ensure a suitable water vapor permeability for suppressing skin rash and other trouble.

In order to make the transdermal patch inconspicuous when it is attached, that is, in order to make it easy to show the skin color beneath the patch through it, a plastic film having excellent transparency is preferably employed. A backing such as fabrics can obtain color that is a little different from skin color by coloring the backing with a coloring agent into a color tone such as a flesh color.

The backing typically has a thickness of about 5 μm to 1 mm. A fabric backing preferably has a thickness of 50 μm to 1 mm, more preferably 100 μm to 800 μm, and even more preferably 200 μm to 700 μm. A plastic film backing preferably has a thickness of 10 μm to 300 μm, more preferably 12 μm to 200 μm, and even more preferably 15 μm to 150 μm. A backing having a very small thickness of about 5 μm to 30 μm is preferably provided with a releasable carrier film layer on a face opposite to the pressure-sensitive adhesive layer or to the rivastigmine-containing layer that is formed on the backing because handling properties as the transdermal patch is improved. A backing having a thickness of less than 5 μm reduces the strength and the handling properties of the transdermal patch, makes attachment to a skin difficult, and may be torn due to the contact with another member, for example, or be peeled off from a skin within a short period due to the contact with water in a bath, for example. A transdermal patch including a backing having an excessively large thickness (more than 1 mm) does not easily follow skin movement and readily form a trigger for peeling-off at the periphery of the transdermal patch. Hence, such a transdermal patch may be peeled off from a skin within a short period or may increase uncomfortable feeling during attachment. In the case of a film backing, one side or both sides of the backing may be subjected to a treatment such as a sandblast treatment and a corona treatment in order to improve anchoring properties between the pressure-sensitive adhesive and the backing. Furthermore, in order to readily take out the transdermal patch from a package, one side or both sides of the backing may be provided with an uneven surface by a method other than the sandblast.

As a backing meeting the conditions such as the water vapor permeability, the transparency, and the thickness, polyester films are preferred and polyethylene terephthalate films are especially preferred.

[Release Liner]

The release liner used in the transdermal patch of the present invention is preferably composed of a material that is unlikely to absorb and adsorb a medicinal agent, for example, in the pressure-sensitive adhesive. Examples of such a material include a polyester film having one side or both sides treated with silicone, a polyethylene laminated high-quality paper treated with silicone, and a glassine paper treated with silicone. The release liner may have an uneven surface in order to easily take out the transdermal patch from a package. The release liner may have, for example, a rectangular shape with rounded corners and a circular shape and has the same size as or a size slightly larger than the size of the backing on which the rivastigmine-containing layer and the pressure-sensitive adhesive layer are provided.

[Method for Producing Transdermal Patch]

The transdermal patch for the treatment of Alzheimer's disease of the present invention can be produced through the steps described in i) or ii) below.

i) A rivastigmine layer formation step of applying a solution containing rivastigmine onto a backing to form a rivastigmine-containing layer, a pressure-sensitive adhesive layer formation step of applying a solution containing an acrylic pressure-sensitive adhesive onto a release liner to form a pressure-sensitive adhesive layer, and a transdermal patch formation step of laminating the rivastigmine-containing layer formed on the backing to the pressure-sensitive adhesive layer formed on the release liner.

ii) A pressure-sensitive adhesive layer formation step of applying a solution containing an acrylic pressure-sensitive adhesive onto a backing to form a pressure-sensitive adhesive layer, a rivastigmine layer formation step of applying a solution containing rivastigmine onto a release liner to form a rivastigmine-containing layer, and a transdermal patch formation step of laminating the pressure-sensitive adhesive layer formed on the backing to the rivastigmine-containing layer formed on the release liner.

Alternatively, the transdermal patch of the present invention can also be produced, for example, through the steps described in iii) below.

iii) A pressure-sensitive adhesive layer formation step of applying a solution containing an acrylic pressure-sensitive adhesive onto a backing to form a pressure-sensitive adhesive layer, a rivastigmine layer formation step of applying a solution containing rivastigmine onto the pressure-sensitive adhesive layer to form a rivastigmine-containing layer, and a transdermal patch formation step of laminating the rivastigmine-containing layer formed on the pressure-sensitive adhesive layer on the backing to a release liner.

The solution containing rivastigmine is a solution containing rivastigmine and an alkyl (meth)acrylate resin. Examples of the alkyl (meth)acrylate resin include the alkyl (meth) acrylate copolymers and the acrylic pressure-sensitive adhesives containing a (meth)acrylic acid ester exemplified above. The solution may further include an additional additive such as a softener (plasticizer) and an inorganic filler.

The solution containing an acrylic pressure-sensitive adhesive contains an acrylic pressure-sensitive adhesive containing a (meth)acrylic acid ester having a hydroxy group. Examples of the pressure-sensitive adhesive include the various pressure-sensitive adhesives exemplified above. The solution may further include an additional additive such as another medical agent, a tackifier, a cross-linking agent, a softener (plasticizer), an absorption enhancer, polyhydric alcohols, silicone oils, an inorganic filler, and an ultraviolet absorber.

Each of the solution containing rivastigmine and the solution containing an acrylic pressure-sensitive adhesive may appropriately include a solvent or the like, considering the operability when such a solution is applied onto the backing, the release liner, and the like. The solvent is not particularly limited as long as the acrylic pressure-sensitive adhesive containing a (meth)acrylic acid ester having a hydroxy group, the rivastigmine, and the alkyl (meth)acrylate resin can be dissolved.

Each of the solution containing rivastigmine and the solution containing an acrylic pressure-sensitive adhesive does not contain an anti-oxidizing agent.

The method for producing a transdermal patch of the present invention is performed, for example, in the procedure below in the case of the process i).

The acrylic pressure-sensitive adhesive containing a (meth)acrylic acid ester having a hydroxy group, and additional components except the medical agent and a solvent (ethyl acetate, ethanol, and hexane, etc.) for dissolving the pressure-sensitive adhesive, if desired, are stirred and mixed at a maximum temperature of room temperature to about 40° C. so as to prepare a pressure-sensitive adhesive solution homogeneously containing the components. The prepared solution is spread on a release liner or a backing with a coater so as to give a thickness of 10 μm to 100 μm after drying the solvent, and then dried at a temperature of 60° C. to 120° C. to form a pressure-sensitive adhesive layer.

Separately, the rivastigmine, the alkyl (meth)acrylate resin, and additional components, if desired, are mixed at a maximum temperature of room temperature or 1° C. or higher and lower than 60° C. to prepare a rivastigmine-containing solution homogeneously containing the components. The prepared solution is spread on a release liner or a backing with a coater so as to give a thickness of 10 μm to 80 μm to form a rivastigmine-containing layer. When an acrylic pressure-sensitive adhesive is used as the alkyl (meth)acrylate resin, a solvent drying step may be included after the spread on the release liner or the backing.

Finally, the pressure-sensitive adhesive layer formed on the release liner or the backing and the rivastigmine-containing layer formed on the backing or the release liner are opposed and laminated to each other, followed by cutting to produce a transdermal patch having two layers composed of the pressure-sensitive adhesive layer containing the acrylic pressure-sensitive adhesive and the rivastigmine-containing layer.

In the transdermal patch of the present invention, from the viewpoint of the stability of the rivastigmine as the active component, it is preferred that the rivastigmine layer formation step described above is performed by a so-called "ointment coating method" in which a mixing step and a drying step are performed at a temperature as low as possible, rather than a calendering method or a hot melting method that is employed for a common transdermal patch production and that includes a heating and kneading (stirring) step or a spread coating method that includes a heating and drying step after coating.

In the present specification, the "ointment coating method" is a method of forming a layer at a low temperature, for example, at a temperature of 1° C. or higher and lower than 60° C., preferably under a temperature condition of 20° C. to 34° C., and more preferably 26° C. to 34° C. In other words, in the present invention, the "ointment coating method" means a method of forming the rivastigmine-containing layer under the temperature condition mentioned above by coating or lamination. The alkyl (meth)acrylate resin in the rivastigmine-containing layer is preferably an alkyl (meth)acrylate copolymer having a weight average molecular weight of 300,000 or less because the coating can be performed at a lower temperature.

In the transdermal patch of the present invention, the pressure-sensitive adhesive layer formation step can be performed by any conventional methods for forming a pressure-sensitive adhesive layer such as a spread coating method, an emulsion method, a hot melting method, and an electron beam curing method. That is, in the present invention, the pressure-sensitive adhesive layer formation step means a step of kneading, stirring, curing, and drying a pressure-sensitive adhesive and the like at a high temperature (for example 60° C. to 180° C.) to form a pressure-sensitive adhesive layer on a backing or a release liner.

Preferably, the method for producing a transdermal patch of the present invention further includes a cooling step of allowing the pressure-sensitive adhesive layer to cool or forced-cooling the pressure-sensitive adhesive layer, after the pressure-sensitive adhesive layer formation step and before the transdermal patch formation step. In other words, it is preferable that a transdermal patch formation step in which the pressure-sensitive adhesive layer is directly brought into contact with the rivastigmine layer be not performed immediately after the formation of the pressure-sensitive adhesive layer but the transdermal patch formation step be performed after cooling the pressure-sensitive adhesive layer.

The reason for this is as follows. The pressure-sensitive adhesive layer formation step is performed at a high temperature. Accordingly, the pressure-sensitive adhesive layer has a very high temperature immediately after the formation of the pressure-sensitive adhesive layer. When such a pressure-sensitive adhesive layer is directly brought into contact with the rivastigmine-containing layer, the rivastigmine layer is heated to so that the temperature of the layer increases, which may affect the stability of the rivastigmine.

Therefore, in the present invention, it is preferable that the rivastigmine layer formation step and the pressure-sensitive adhesive layer formation step be not performed in an integrated system, that is, these steps do not proceed at the same time and are separately performed (in a non-integrated system).

A specific example of the procedure for the non-integrated system will be described below.

First, when the pressure-sensitive adhesive layer formation step is performed by, for example, a spread coating method, a pressure-sensitive adhesive is diluted with a solvent such as toluene, hexane, ethyl acetate, and ethanol and is spread on a backing or a release liner. The solvent is evaporated at a high temperature (for example 120° C.), and a pressure-sensitive adhesive layer is formed on the backing or the release liner. A plurality of layers containing the pressure-sensitive adhesive layer and the backing or containing the pressure-sensitive adhesive layer and the release liner obtained by the formation step are defined as a bulk tape. In the bulk tape, on the assumption that it is left standing for a predetermined period of time for the temperature decrease as described later, a release sheet that is removed at the transdermal patch formation step may be laminated on the pressure-sensitive adhesive layer provided on the backing or the release liner, in order to suppress drying of the pressure-sensitive adhesive layer or to avoid contamination. Examples of the material for the release sheet include those exemplified for the release liner above.

After the preparation of the bulk tape, a cooling step of cooling the bulk tape to reduce the temperature is provided after the pressure-sensitive adhesive layer formation step and the temperature of the bulk tape is reduced to about room temperature. Examples of the temperature control (cool) means used for the cooling step include a method of bringing the bulk tape into contact with a water cooled roll at a low temperature, a method of applying an air flow at a low temperature to the bulk tape, and a method of winding the bulk tape onto a roll and then leaving the bulk tape standing at room temperature for a predetermined period of time for cooling (allowing the bulk tape to cool). The production method may further include an aging step for an aging period under a certain condition (40° C. to 50° C., one day to two weeks) before and after the cooling step. Through the aging step, the bulk tape obtains increased cohesiveness to achieve stable adhesive power.

Using the bulk tape that is allowed to cool to about room temperature and, if possible, left at room temperature for several days as above, the rivastigmine layer formation step and the transdermal patch formation step are performed in another working environment equipped with an air conditioning apparatus capable of setting the environment at a low temperature (preferably 20° C. to 34° C. and more preferably 26° C. to 34° C.). In the transdermal patch formation step, the temperature of the bulk tape may be controlled at, for example, 10° C. to 40° C., preferably 20° C. to 34° C., and more preferably 26° C. to 34° C., using the temperature control means. The temperature in each step can be ascertained by means such as a contact thermometer, a non-contact room thermometer, and an infrared thermo sensor.

In this manner, by controlling the temperature of the bulk tape and each temperature in the rivastigmine layer formation step and the transdermal patch formation step, the lamination of the bulk tape and the rivastigmine layer is smoothly performed and the two layers are readily integrated. However, it should be noted that when the lamination is performed at room temperature or below (less than 20° C.), the produced transdermal patch may be separated into two layers when such a transdermal patch is applied onto a skin and the pressure-sensitive adhesive layer is likely to remain on a skin side.

In the production method, the pressure-sensitive adhesive layer formation step and the rivastigmine layer formation step are not performed at the same time, and the transdermal patch formation step is performed a predetermined time after the pressure-sensitive adhesive layer formation step. This facilitates the control of the temperature in each working environment as well as can diversify or reduce the risk when malfunction occurs in the steps.

By bringing the pressure-sensitive adhesive layer into contact with the rivastigmine-containing layer, the rivastigmine serving as the active component is permeated and diffused from the rivastigmine-containing layer into the pressure-sensitive adhesive layer. Thus, a transdermal patch is obtained that includes two layers composed of the rivastigmine layer and the pressure-sensitive adhesive layer in which the active component is substantially equally contained. For example, with respect to a pressure-sensitive adhesive layer having a thickness of 10 μm to 100 μm, the rivastigmine-containing layer is brought into contact by coating or lamination to produce a transdermal patch. Then, the transdermal patch is subjected to aging under a low temperature condition (1° C. or more and less than 50° C.) for a day to about two weeks. Thus, the transdermal patch having the pressure-sensitive adhesive layer in which the rivastigmine is evenly diffused and permeated can be obtained.

It is preferred that the transdermal patch of the present invention produced as above is enclosed in a package prepared from a packing material having high sealing performance and high light blocking performance and stored until immediately before the use.

For the packing material having high sealing performance and high light blocking performance used for the package, a material commonly used for the package of a transdermal patch can be used. Examples of the packing material having high sealing performance include polyolefin resin films such as polyethylene films, polypropylene films, and polymethylpentene films; vinyl resin films such as polyvinyl chloride films, polyvinylidene chloride films, polyvinyl alcohol films, polystyrene films, polyacrylonitrile films, and ionomer films; polyester resin films such as polyethylene terephthalate films; polyamide resin films such as nylon films; cellulose resin films such as cellophane; polycarbonate resin films; and lamination films of them. Examples of the packing material having high light blocking performance in addition to the high sealing performance include: lamination films of aluminum and the resin film above or a lamination film of the resin films; and pigment-added resin films that is obtained by adding a black pigment, for example, to the resin film above. These resin films, lamination films, and the like may be used in various combinations as a laminate.

The transdermal patch is enclosed in the package prepared from the laminate, then the package can be sealed for storage by a known method such as heat sealing.

In particular, the innermost layer of the package is preferably a layer having no adsorptive property with respect to the rivastigmine. For example, polyacrylonitrile is preferably used as the innermost layer.

The package preferably has a film or a sheet that includes a layer containing an oxygen adsorber from the viewpoint of the stability of the rivastigmine. Examples of the oxygen absorber include, but are not necessarily limited to, inorganic oxides such as cesium oxide, zinc oxide, titanium dioxide, and iron oxide; mixtures composed of a powder of iron such as iron and iron carbide and an electrolyte such as halogenated metal salts; reducing inorganic salts such as sulfite salts, thiosulfate salts, and ferrous salts; polyphenols such as hydroquinone, catechol, resorcin, and pyrogallol; reducing sugars such as glucose; any composition containing a reducing agent including reducing higher alcohols such as ascorbic acid and erythorbic acid as a main active component; compositions containing an unsaturated organic compound such as unsaturated fatty acid compounds and chain hydrocarbon polymers having an unsaturated group or a thermoplastic polymer such as polyamides and polyolefins as a main component and containing an oxygen absorption promoting substance such as transition-metal salts; and mixtures of them. Examples of the packing material containing an oxygen absorber include Oxyguard (registered trademark) (manufactured by Toyo Seikan Kaisha, Ltd.) and OxyCatch (registered trademark) (manufactured by Kyodo Printing Co., Ltd.). The oxygen absorber may be separately enclosed in a package as well as contained in the package (in a packing material).

It is particularly preferable that an atmosphere in the package be substituted and filled with nitrogen with a vacuum gas packaging machine or the like after the transdermal patch is enclosed in the package, from the viewpoint of the stability of the rivastigmine.

The transdermal patch of the present invention obtained as above has an advantage of excellent temporal stability of the rivastigmine. For example, the transdermal patch of the present invention includes degradation products of the rivastigmine in a total amount of less than 0.2% by mass immediately after the production based on the amount of the rivastigmine, and includes the degradation products in a total amount of less than 0.50% by mass and preferably less than 0.35% by mass after storage under a severe condition (60° C.) for two weeks based on the amount of the rivastigmine.

EXAMPLES

Hereinafter, the present invention will be described in further detail with reference to examples; however, the present invention is not limited to these examples.

<Production of Transdermal Patch (1)>

Example 1

Production of Transdermal Patch by Ointment Coating Method (1)

At room temperature, 40% by mass of DURO-TAK (registered trademark) 87-2516 (containing a hydroxy group, Henkel) as an acrylic pressure-sensitive adhesive and 60% of ethyl acetate were mixed to prepare an acrylic pressure-sensitive adhesive solution (the value (%) is based on the total mass of the pressure-sensitive adhesive solution). Next, the solution was applied onto a silicone release-treated PET film (FILMBYNA (registered trademark) 75E-0010 No. 23, manufactured by Fujimori Kogyo Co., Ltd.) having a thickness of 75 μm so as to give a thickness of 80 μm after drying, and the coated film was dried at 60° C. to 100° C. to form a pressure-sensitive adhesive layer.

Each of 90% by mass of rivastigmine and 10% by mass of Eudragit (registered trademark) EPO (Evonik Degussa) was weighed, charged in a glass bottle, and dissolved at room temperature so that a rivastigmine solution (the value (%) is based on the total mass of the rivastigmine solution) was obtained. The obtained rivastigmine solution was applied onto a PET film (LUMIRROR (registered trademark) S 10, manufactured by Toray Industries Inc.) having a thickness of 25 µm as a backing so as to give a thickness of 20 µm to form a rivastigmine-containing layer.

The pressure-sensitive adhesive layer formed on the silicone release-treated PET film and the rivastigmine-containing layer formed on the PET film were opposed and laminated to each other to produce a transdermal patch having two layers of the pressure-sensitive adhesive layer containing the acrylic pressure-sensitive adhesive and the rivastigmine-containing layer.

The produced preparation was sealed in an aluminum package having the innermost layer mainly composed of polyacrylonitrile, and nitrogen substitution in the package was carried out using a vacuum gas packaging machine.

Comparative Example 1

Production of Transdermal Patch by Ointment Coating Method (2)

A transdermal patch was produced in the same manner as in Example 1 except that DURO-TAK (registered trademark) 87-2194 (containing a carboxy group, Henkel) was used as an acrylic pressure-sensitive adhesive in place of DURO-TAK (registered trademark) 87-2516 (Henkel) and the pressure-sensitive adhesive layer had a thickness of 60 µm after drying.

Comparative Example 2

Production of Transdermal Patch by Ointment Coating Method (3)

A transdermal patch was produced in the same manner as in Example 1 except that DURO-TAK (registered trademark) 87-2516 (containing a hydroxy group, Henkel) and DURO-TAK (registered trademark) 87-2194 (containing a carboxy group, Henkel) were used in combination in equivalent amounts as acrylic pressure-sensitive adhesives in place of DURO-TAK (registered trademark) 87-2516 (Henkel) alone and the pressure-sensitive adhesive layer had a thickness of 60 µm after drying.

Comparative Example 3

Production of Transdermal Patch by Spread Coating Method (1)

In accordance with the formulation of 75.0% by mass of DURO-TAK (registered trademark) 87-2516 (containing a hydroxy group, Henkel) as an acrylic pressure-sensitive adhesive, 2.5% by mass of Eudragit (registered trademark) EPO, and 22.5% by mass of rivastigmine (the value (%) is based on the total mass of the pressure-sensitive adhesive layer), the components were mixed, and diluted with ethyl acetate so as to give a solid content of 35% to 40%, and the mixture was stirred at room temperature (about 25° C.) to prepare a homogeneous pressure-sensitive adhesive solution.

Next, the pressure-sensitive adhesive solution was spread on a silicone release-treated PET film (FILMBYNA (registered trademark) 75E-0010 No. 23, manufactured by Fujimori Kogyo Co., Ltd.) having a thickness of 75 µm so as to give a thickness of 80 µm after drying, and the coated film was dried at 60° C. to 100° C. to form a pressure-sensitive adhesive layer. Onto the pressure-sensitive adhesive layer, a PET film (LUMIRROR (registered trademark) S10, manufactured by Toray Industries Inc.) having a thickness of 25 µm was laminated as a backing to produce a transdermal patch. The transdermal patch includes one layer of the pressure-sensitive adhesive layer containing the acrylic pressure-sensitive adhesive and the rivastigmine between the backing and the release liner.

The produced preparation was sealed in an aluminum package having the innermost layer mainly composed of polyacrylonitrile, and nitrogen substitution in the package was carried out using a vacuum gas packaging machine.

Comparative Example 4

Production of Transdermal Patch by Spread Coating Method (2)

A transdermal patch was produced in the same manner as in Comparative Example 3 except that DURO-TAK (registered trademark) 87-2194 (containing a carboxy group, Henkel) was used as an acrylic pressure-sensitive adhesive in place of DURO-TAK (registered trademark) 87-2516 (Henkel). The transdermal patch includes one layer of the pressure-sensitive adhesive layer containing the acrylic pressure-sensitive adhesive and the rivastigmine between the backing and the release liner.

Comparative Example 5

Production of Transdermal Patch by Spread Coating Method (3)

A transdermal patch was produced in the same manner as in Comparative Example 3 except that DURO-TAK (registered trademark) 87-2516 (containing a hydroxy group, Henkel) and Durotak 87-2194 (containing a carboxy group, Henkel) were used in combination in equivalent amounts as acrylic pressure-sensitive adhesives in place of DURO-TAK (registered trademark) 87-2516 (Henkel) alone. The transdermal patch includes one layer of the pressure-sensitive adhesive layer containing the acrylic pressure-sensitive adhesive and the rivastigmine between the backing and the release liner.

<Stability Evaluation of Transdermal Patch (1)
(1) Amount of Degradation Product Contained Immediately After Production of Transdermal Patch The total amount (% by mass) of degradation products contained was measured immediately after the production in accordance with the following procedure, in each transdermal patch produced in Example 1 and Comparative Example 1 to Comparative Example 5.

The obtained results are shown in Table 1.

[Measurement Procedure for Amount of Degradation Product Contained]

The measurement method of the amount of degradation products contained was as follows. That is, the release liner of the transdermal patch was removed; the transdermal patch was immersed in a sealable glass container containing tetrahydrofuran to dissolve the pressure-sensitive adhesive; then purified water was added to the solution; and the diluted solution was analyzed by high performance liquid chromatography (HPLC). The amount of degradation products contained was determined in accordance with the formula below. The peak area of each degradation product was calculated with respect to the peak area of the rivastigmine, and the total sum of the peak areas of the degradation products was calculated as the total amount (%) of the degradation products.

Amount of degradation products contained(%)=[peak area of degradation products/peak area of rivastigmine]×100

TABLE 1

| | Pressure-sensitive adhesive | | | | | |
|---|---|---|---|---|---|---|
| | Containing OH group | | Containing COOH group | | Containing OH group/ COOH group | |
| | Coating method | | | | | |
| | Ointment coating | Spread coating | Ointment coating | Spread coating | Ointment coating | Spread coating |
| | Transdermal patch No. | | | | | |
| | Example 1 | Comparative Example 3 | Comparative Example 1 | Comparative Example 4 | Comparative Example 2 | Comparative Example 5 |
| Total amount of degradation products* | 0.191 | 0.783 | 0.126 | 0.310 | 0.146 | 0.439 |

*Each value represents an amount in terms of % by mass with respect to rivastigmine.

As shown in Table 1, in each transdermal patch using the acrylic pressure-sensitive adhesive containing a hydroxy group, the acrylic pressure-sensitive adhesive containing a carboxy group, or the acrylic pressure-sensitive adhesives containing a hydroxy group and a carboxy group, the obtained results revealed that each transdermal patch (Example 1, Comparative Example 1, and Comparative Example 2) produced by the ointment coating method contained the degradation products in a very small amount, as compared with that of each transdermal patch (Comparative Example 3, Comparative Example 4, and Comparative Example 5) produced by the spread coating method.

(2) Change in Total Amount of Degradation Products after Storage of Transdermal Patch Under Severe Condition (1)

The total amount of degradation products was measured after the storage under a severe condition (60° C.) for a week and two weeks in accordance with [Measurement Procedure for Amount of Degradation Product Contained] above, in each transdermal patch produced in Example 1, Comparative Example 1, Comparative Example 3, and Comparative Example 4.

The obtained results are shown in Table 2 and Table 3.

TABLE 2

| | Pressure-sensitive adhesive Acrylic pressure-sensitive adhesive containing OH group | | | | | |
|---|---|---|---|---|---|---|
| | Transdermal patch No./coating method | | | | | |
| | Example 1/ointment coating | | | Comparative Example 3/spread coating | | |
| | Time course | | | | | |
| | Immediately after production | After a week | After two weeks | Immediately after production | After a week | After two weeks |
| Total amount of degradation products* | 0.191 | 0.280 | 0.345 | 0.783 | 0.946 | 1.104 |
| Change in amount (slope)** | | 0.0772 | | | 0.1607 | |

*Each value represents an amount in terms of % by mass with respect to rivastigmine.
**The slope of an approximate line determined from plots of the total amount of degradation products with respect to the time course

TABLE 3

| | Pressure-sensitive adhesive Acrylic pressure-sensitive adhesive containing COOH group | | | | | |
|---|---|---|---|---|---|---|
| | Transdermal patch No./coating method | | | | | |
| | Comparative Example 1/ointment coating | | | Comparative Example 4/spread coating | | |
| | Time course | | | | | |
| | Immediately after production | After a week | After two weeks | Immediately after production | After a week | After two weeks |
| Total amount of degradation products* | 0.126 | 0.454 | 0.682 | 0.310 | 0.776 | 1.388 |
| Change in amount (slope)** | | 0.2780 | | | 0.5389 | |

*Each value represents an amount in terms of % by mass with respect to rivastigmine.
**The slope of an approximate line determined from plots of the total amount of degradation products with respect to the time course As shown in Table 2 and Table 3, in each transdermal patch using the acrylic pressure-sensitive adhesive containing a hydroxy group or the acrylic pressure-sensitive adhesive containing a carboxy group, the obtained results revealed that each transdermal patch (Example 1 and Comparative Example 1) produced by the ointment coating method contained the degradation products in a very small amount, as compared with that of each transdermal patch (Comparative Example 3 and Comparative Example 4) produced by the spread coating method after the storage for two weeks.

In the transdermal patches produced by the ointment coating method, the obtained results revealed that the transdermal patch (Example 1) using the acrylic pressure-sensitive adhesive containing a hydroxy group contained the degradation products in an amount smaller than that of the transdermal patch (Comparative Example 1) using the acrylic pressure-sensitive adhesive containing a carboxy group after the storage for two weeks.

The changes with time in the total amount of degradation products contained were compared as the slope of an approximate line determined from plots of the total amount of degradation products with respect to the time course. The obtained results revealed that the transdermal patch using the hydroxy-containing acrylic pressure-sensitive adhesive and produced by the ointment coating method had the smallest slope, that is, had the smallest change with time in the total amount of degradation products and had high stability.

<Production of Transdermal Patch (2)>

Example 2

A transdermal patch was produced in the same manner as in Example 1 except that the pressure-sensitive adhesive layer had a thickness of 60 μm.

Example 3

A transdermal patch was produced in the same manner as in Example 1 except that DURO-TAK (registered trademark) 87-2287 (containing a hydroxy group, Henkel) was used as an acrylic pressure-sensitive adhesive in place of DURO-TAK (registered trademark) 87-2516 (Henkel) and the pressure-sensitive adhesive layer had a thickness of 60 μm.

Comparative Example 6

A transdermal patch was produced in the same manner as in Example 1 except that MAS683 (acrylic pressure-sensitive adhesive containing a pyrrolidone ring, CosMED Pharmaceutical Co. Ltd.) was used as an acrylic pressure-sensitive adhesive in place of DURO-TAK (registered trademark) 87-2516 (Henkel) and the pressure-sensitive adhesive layer had a thickness of 60 μm.

Comparative Example 7

Commercial Product

In Comparative Example 7, RIVASTACH (registered trademark) Patch 18 mg (manufactured by Ono Pharmaceutical Co., Ltd.) that is a commercially available transdermal patch containing the rivastigmine was used.

<Stability Evaluation of Transdermal Patch (2)>

(3) Change in Total Amount of Degradation Products after Storage of Transdermal Patch Under Severe Condition (2)

The total amount of degradation products contained was measured immediately after the production and after the storage under a severe condition (60° C.) for a week and two weeks in accordance with [Measurement Procedure for Amount of Degradation Product Contained] above, in each transdermal patch produced in Example 2, Example 3, Comparative Example 6, and Comparative Example 7.

The obtained results are shown in Table 4 and Table 5.

TABLE 4

| | Pressure-sensitive adhesive | | | | | | | | |
|---|---|---|---|---|---|---|---|---|---|
| | Acrylic pressure-sensitive adhesive containing OH group | | | | | | | | |
| | Transdermal patch No. | | | | | | | | |
| | Example 1 (shown again) | | | Example 2 | | | Example 3 | | |
| | Time course | | | | | | | | |
| | Immediate | 1 week | 2 weeks | Immediate | 1 week | 2 weeks | Immediate | 1 week | 2 weeks |
| Total amount of degradation products* | 0.191 | 0.280 | 0.345 | 0.145 | 0.324 | 0.288 | 0.142 | 0.218 | 0.229 |
| Change in amount (slope)** | | 0.0772 | | | 0.0717 | | | 0.0432 | |

*Each value represents an amount in terms of % by mass with respect to rivastigmine.
**The slope of an approximate line determined from plots of the total amount of degradation products with respect to the time course

TABLE 5

| | Pressure-sensitive adhesive | | | | | | | | |
|---|---|---|---|---|---|---|---|---|---|
| | Acrylic pressure-sensitive adhesive containing COOH group | | | Pyrrolidone pressure-sensitive adhesive | | | Commercial product: RIVASTACH | | |
| Transdermal patch No. | Comparative Example 1 (shown again) | | | Comparative Example 6 | | | Comparative Example 7 | | |
| | | | | Time course | | | | | |
| | Immediate | 1 week | 2 weeks | Immediate | 1 week | 2 weeks | Immediate | 1 week | 2 weeks |
| Total amount of degradation products* | 0.126 | 0.454 | 0.682 | 0.550 | 0.722 | 0.722 | 0.169 | 0.322 | 0.376 |
| Change in amount (slope)** | | 0.2780 | | | 0.0858 | | | 0.1033 | |

*Each value represents an amount in terms of % by mass with respect to rivastigmine.
**The slope of an approximate line determined from plots of the total amount of degradation products with respect to the time course As shown in Table 4 and Table 5, the obtained results revealed that each transdermal patch (Example 1 to Example 3) using the acrylic pressure-sensitive adhesive containing a hydroxy group contained the degradation products in an amount (total amount) smaller than those of each transdermal patch (Comparative Example 1 and Comparative Example 6) using a pressure-sensitive adhesive other than the acrylic pressure-sensitive adhesive containing a hydroxy group and of the commercially available transdermal patch (Comparative Example 7) after the storage for two weeks.

Also in the change with time in the total amount of degradation products contained that was calculated as the slope of an approximate line determined from plots of the total amount of degradation products with respect to the time course, the obtained results revealed that each transdermal patch (Example 1 to Example 3) using the acrylic pressure-sensitive adhesive containing a hydroxy group had a slope smaller than those of the other transdermal patches and had high stability.

<Performance Evaluation of Transdermal Patch>

Using each transdermal patch of Example 1 and Comparative Example 3, the holding force to a glass plate and the probe tack were measured in accordance with the following procedures.

(1) Holding Power with Respect to Glass Plate

The measurement of holding power with respect to a glass plate was carried out in accordance with JIS Z-0237. A sample having a width of 12 mm was laminated to a glass plate so as to give an area of 12 mm×20 mm at a temperature of 23° C. in an atmosphere of 50% RH, and was pressed for laminating by one set of reciprocal movement of a 2-kg rubber roller at a speed of 300 mm/min. After the sample was left standing for 20 minutes, the pressure-sensitive adhesive sheet was vertically hung, then a load of 100 g was applied to the sheet, and the displaced length was measured after 15 minutes and 30 minutes. The obtained results are shown in Table 6.

(2) Probe Tack

The measurement of probe tack was carried out in accordance with Reference 5 in JIS Z-0237 (1991). Using a probe tack tester from Nichiban, a smooth leading end face of a metal cylindrical probe having a diameter of 5 mm was laminated to a surface of a pressure-sensitive adhesive at a temperature of 23° C. in an atmosphere of 50% RH while applying a load of 0.98 N/cm² (100±1 gf/cm²) for 1.0±0.1 second, and the resistance value was measured when the probe was peeled at 10±0.1 mm per second. The obtained results are shown in Table 6.

TABLE 6

| Pressure-sensitive adhesive | | Acrylic pressure-sensitive adhesive containing OH group | |
|---|---|---|---|
| Coating method | | Ointment coating | Spread coating |
| Transdermal patch No. | | Example 1 | Comparative Example 3 |
| Holding power with respect to glass plate (mm/12 × 20 mm, load 100 g) | After 15 minutes | 0.9 | 2.1 |
| | After 30 minutes | 2.1 | Fallen |
| Probe tack (N/5 mm Φ) | | 5.54 | 5.10 |

As shown in Table 6, the obtained results revealed that the transdermal patch of Example 1 produced by the ointment coating method had a holding power with respect to a glass plate and a probe tack which are both better than those of the transdermal patch of Comparative Example 3 produced by the solvent coating method.

<Production of Transdermal Patch (3)>

Example 4

A transdermal patch was produced in the same manner as in Example 1 except that DURO-TAK (registered trademark) 87-2287 (containing a hydroxy group, Henkel) was used as an acrylic pressure-sensitive adhesive in place of DURO-TAK (registered trademark) 87-2516 (Henkel), the pressure-sensitive adhesive layer had a thickness of 60 μm, and the nitrogen substitution was not performed after the sealing of the produced preparation in a package.

Comparative Example 8

A transdermal patch was produced in the same manner as in Example 1 except that MAS683 (acrylic pressure-sensitive adhesive containing a pyrrolidone ring, CosMED Pharmaceutical Co. Ltd.)) was used as an acrylic pressure-sensitive adhesive in place of DURO-TAK (registered trademark) 87-2516 (Henkel), the pressure-sensitive adhesive layer had a thickness of 60 μm, and the nitrogen substitution was not performed after the sealing of the produced preparation in a package.

<Stability Evaluation of Transdermal Patch (3)>
(4) Change in Total Amount of Degradation Products after Storage of Transdermal Patch Under Severe Condition (3)

The total amount of degradation products was measured in accordance with [Measurement Procedure for Amount of Degradation Product Contained] above immediately after the production and after the storage under a severe condition (60° C.) for two weeks, in each transdermal patch produced in Example 4 and Comparative Example 8.

The obtained results are shown in Table 7.

<Production of Transdermal Patch (4)>

Example 5

A transdermal patch was produced in the same manner as in Example 1 except that DURO-TAK (registered trademark) 87-2516 (containing a hydroxy group, Henkel) and DURO-TAK (registered trademark) 87-2287 (containing a hydroxy group, Henkel) were used in combination in equivalent amounts as acrylic pressure-sensitive adhesives in place of DURO-TAK (registered trademark) 87-2516 (Henkel) alone and the produced preparation was sealed in OxyCatch (registered trademark) (manufactured by Kyodo Printing Co., Ltd.) as a package containing an oxygen absorber in place of the aluminum package having the innermost layer mainly composed of polyacrylonitrile.

<Stability Evaluation of Transdermal Patch (4)>

TABLE 7

| | Pressure-sensitive adhesive | | | | |
|---|---|---|---|---|---|
| | Acrylic pressure-sensitive adhesive containing OH group | | Pyrrolidone pressure-sensitive adhesive | | (reference) RIVASTACH |
| | Transdermal patch No. | | | | |
| | Example 3 (shown again) | Example 4 | Comparative Example 6 (shown again) | Comparative Example 8 | Comparative Example 7 (shown again) |
| | Nitrogen substitution | | | | |
| | Performed | Not performed | Performed | Not performed | — |
| | Time course | | | | |
| | Immediate  2 weeks | Immediate  2 weeks | Immediate  2 weeks | Immediate  2 weeks | Immediate  2 weeks |
| Total amount of degradation products* | 0.142   0.229 | 0.097   0.476 | 0.550   0.722 | 0.716   1.195 | 0.169   0.376 |
| Change in amount (slope)** | 0.0432 | 0.1895 | 0.0858 | 0.2395 | 0.1033 |

*Each value represents an amount in terms of % by mass with respect to rivastigmine.
**The slope of an approximate line determined from plots of the total amount of degradation products with respect to the time course As shown in Table 7, the obtained results revealed that by sealing the produced preparation in the aluminum package having the innermost layer mainly composed of polyacrylonitrile, and then performing the nitrogen substitution in the package using a vacuum gas packaging machine, it is possible to provide a transdermal patch having a smaller amount (total amount) of degradation products contained after the storage for two weeks, having a smaller change with time in the total amount of degradation products contained that is calculated as the slope of an approximate line determined from plots of the total amount of degradation products with respect to the time course, and having higher stability.

(5) Change in Total Amount of Degradation Products after Storage of Transdermal Patch Under Severe Condition (4)

The total amount of degradation products was measured in accordance with [Measurement Procedure for Amount of Degradation Product Contained] above immediately after the production and after the storage under a severe condition (60° C.) for a week, in the transdermal patch produced in Example 5.

The obtained results are shown in Table 8.

TABLE 8

| Pressure-sensitive adhesive Transdermal patch No. | Acrylic pressure-sensitive adhesive containing OH group Example 5 | | (reference) RIVASTACH Comparative Example 7 (shown again) | |
|---|---|---|---|---|
| Time course | Immediate | 1 week | Immediate | 1 week |
| Total amount of degradation products* | 0.185 | 0.273 | 0.169 | 0.322 |
| Change in amount (slope)** | 0.0880 | | 0.1033 | |

*Each value represents an amount in terms of % by mass with respect to rivastigmine.
**The slope of an approximate line determined from plots of the total amount of degradation products with respect to the time course As shown in Table 8, the obtained results revealed that the sealing of the produced preparation in the package containing the oxygen absorber in place of the aluminum package having the innermost layer mainly composed of polyacrylonitrile can produce the transdermal patch having further improved stability.

The invention claimed is:

1. A transdermal patch for treatment of Alzheimer's disease, comprising:
a backing;
a rivastigmine-containing layer provided on the backing;
a pressure-sensitive adhesive layer provided on the rivastigmine-containing layer; and
a release liner, or comprising:
a backing;
a pressure-sensitive adhesive layer provided on the backing;
a rivastigmine-containing layer provided on the pressure-sensitive adhesive layer; and
a release liner, wherein
the rivastigmine-containing layer contains rivastigmine and an alkyl (meth)acrylate resin,
the pressure-sensitive adhesive layer is composed of an acrylic pressure-sensitive adhesive containing a (meth)acrylic acid ester having a hydroxy group, wherein the pressure-sensitive adhesive layer does not contain an acrylic pressure-sensitive adhesive containing a (meth)acrylic acid ester having carboxy group, and
neither the rivastigmine-containing layer nor the pressure-sensitive adhesive layer contains an anti-oxidizing agent.

2. The transdermal patch for treatment of Alzheimer's disease according to claim 1, wherein the rivastigmine-containing layer is a layer formed by using a solution containing the rivastigmine under a condition at 1° C. or higher and lower than 60° C.

3. The transdermal patch for treatment of Alzheimer's disease according to claim 1, wherein the rivastigmine-containing layer contains the rivastigmine in an amount of 20% to 95% by mass based on a total mass of the layer.

4. The transdermal patch for treatment of Alzheimer's disease according to claim 1, wherein the rivastigmine-containing layer is a layer having a thickness of 10 μm to 80 μm and the pressure-sensitive adhesive layer is a layer having a thickness of 10 μm to 100 μm.

5. A method for producing a transdermal patch for treatment of Alzheimer's disease, the method comprising:
a rivastigmine layer formation step of applying a solution containing rivastigmine onto a backing to form a rivastigmine-containing layer;
a pressure-sensitive adhesive layer formation step of applying a solution containing an acrylic pressure-sensitive adhesive onto a release liner to form a pressure-sensitive adhesive layer; and
a transdermal patch formation step of laminating the rivastigmine-containing layer formed on the backing to the pressure-sensitive adhesive layer formed on the release liner, wherein
the solution containing rivastigmine contains the rivastigmine and an alkyl (meth)acrylate resin,
the solution containing an acrylic pressure-sensitive adhesive contains an acrylic pressure-sensitive adhesive containing a (meth)acrylic acid ester having a hydroxy group, wherein the pressure-sensitive adhesive layer does not contain an acrylic pressure-sensitive adhesive containing a meth acrylic acid ester having a carboxy group, and
neither the solution containing rivastigmine nor the solution containing an acrylic pressure-sensitive adhesive contains an anti-oxidizing agent.

6. A method for producing a transdermal patch for treatment of Alzheimer's disease, the method comprising:
a pressure-sensitive adhesive layer formation step of applying a solution containing an acrylic pressure-sensitive adhesive onto a backing to form a pressure-sensitive adhesive layer;
a rivastigmine layer formation step of applying a solution containing rivastigmine onto a release liner to form a rivastigmine-containing layer: and
a transdermal patch formation step of laminating the pressure-sensitive adhesive layer formed on the backing to the rivastigmine-containing layer formed on the release liner, wherein
the solution containing rivastigmine contains the rivastigmine and an alkyl (meth)acrylate resin,
the solution containing an acrylic pressure-sensitive adhesive contains an acrylic pressure-sensitive adhesive containing a (meth)acrylic acid ester having a hydroxy group, wherein the pressure-sensitive adhesive layer does not contain an acrylic pressure-sensitive adhesive containing a (meth)acrylic acid ester having a carboxy group, and
neither the solution containing rivastigmine nor the solution containing an acrylic pressure-sensitive adhesive contains an anti-oxidizing agent.

7. A method for producing a transdermal patch for treatment of Alzheimer's disease, the method comprising:
a pressure-sensitive adhesive layer formation step of applying a solution containing an acrylic pressure-sensitive adhesive onto a backing to form a pressure-sensitive adhesive layer;
a rivastigmine layer formation step of applying a solution containing rivastigmine onto the pressure-sensitive adhesive layer to form a rivastigmine-containing layer; and
a transdermal patch formation step of laminating the rivastigmine-containing layer formed on the pressure-sensitive adhesive layer on the backing to a release liner, wherein
the solution containing rivastigmine contains the rivastigmine and an alkyl (meth)acrylate resin,
the solution containing an acrylic pressure-sensitive adhesive contains an acrylic pressure-sensitive adhesive containing a (meth)acrylic acid ester having a hydroxy group, wherein the pressure-sensitive adhesive layer does not contain an acrylic pressure-sensitive adhesive containing a (meth)acrylic acid ester having a carboxy group, and
neither the solution containing rivastigmine nor the solution containing an acrylic pressure-sensitive adhesive contains an anti-oxidizing agent.

8. The method according to claim 5, wherein the rivastigmine layer formation step comprises applying the solution containing rivastigmine under a temperature condition of 1° C. or higher and lower than 60° C.

9. The method according to claim 5, further comprising a cooling step of allowing the pressure-sensitive adhesive layer to cool or forced-cooling the pressure-sensitive adhesive layer, after the pressure-sensitive adhesive layer formation step and before the transdermal patch formation step.

10. The method according to claim 9, further comprising an aging step before and after the cooling step.

11. A product of a transdermal patch for treatment of Alzheimer's disease produced by sealing the transdermal patch for treatment of Alzheimer's disease according to claim 1 in a package composed of a laminate of multi-layered films or multi-layered sheets, wherein an innermost layer of the package is a layer containing polyacrylonitrile as a main component.

12. A product of a transdermal patch for treatment of Alzheimer's disease produced by sealing the transdermal patch for treatment of Alzheimer's disease according to claim 1 in a package composed of a laminate of multi-layered films or multi-layered sheets, wherein the package comprising a film or a sheet including a layer containing an oxygen absorber or an oxygen absorber is separately enclosed in the package.

13. A product of a transdermal patch for treatment of Alzheimer's disease produced by sealing the transdermal patch for treatment of Alzheimer's disease according to claim 1 in a package composed of a laminate of multi-layered films or multi-layered sheets, wherein an atmosphere in the package is substituted and filled with nitrogen.

14. A transdermal patch for treatment of Alzheimer's disease comprising:

a polyester film backing;
a rivastigmine-containing layer provided on the backing;
a pressure-sensitive adhesive layer provided on the rivastigmine-containing layer; and
a release liner, wherein
the rivastigmine-containing layer contains rivastigmine and an alkyl (meth)acrylate resin,
the pressure-sensitive adhesive layer includes an acrylic pressure-sensitive adhesive containing a (meth)acrylic acid ester having a hydroxy group, wherein the pressure-sensitive adhesive layer does not contain an acrylic pressure-sensitive adhesive containing a (meth)acrylic acid ester having a carboxy group,
each of the rivastigmine-containing layer and the pressure-sensitive adhesive layer does not contain an anti-oxidizing agent, and
the transdermal patch includes a degradation product of the rivastigmine in a total amount of less than 0.50% by mass based on an amount of the rivastigmine after storage under a condition of 60° C. for two weeks from a production date of the transdermal patch.

* * * * *